United States Patent [19]

Okitsu

[11] Patent Number: 4,843,083
[45] Date of Patent: * Jun. 27, 1989

[54] 2-PYRIDYLACETIC ACID DERIVATIVE, AND PHARMACEUTICAL COMPOSITION CONTAINING THE SAME AND METHOD OF TREATING A PEPTIC ULCER

[75] Inventor: Mitsuhito Okitsu, Osaka, Japan

[73] Assignee: Suntory Limited, Osaka, Japan

[ * ] Notice: The portion of the term of this patent subsequent to Apr. 19, 2005 has been disclaimed.

[21] Appl. No.: 163,711

[22] Filed: Mar. 3, 1988

Related U.S. Application Data

[63] Continuation-in-part of Ser. No. 925,175, Oct. 31, 1986, Pat. No. 4,738,977.

[30] Foreign Application Priority Data

Nov. 8, 1985 [JP] Japan ................. 60-248970

[51] Int. Cl.$^4$ ................. C07D 213/55; C07D 401/06; A61K 31/445
[52] U.S. Cl. ................. 514/318; 546/267; 546/193; 546/194; 546/331; 514/332; 514/357
[58] Field of Search ............... 546/331, 193, 194, 267; 514/357, 318, 332

[56] References Cited

U.S. PATENT DOCUMENTS 4,738,977  4/1988  Okitsu ................. 514/357

FOREIGN PATENT DOCUMENTS 2215210  8/1974  France ................. 546/331
1147068  4/1969  United Kingdom ........ 546/341

OTHER PUBLICATIONS

Smith, The Chemistry of Open–Chain Organic Nitrogen Compounds, vol. 1, pp. 29–30, Benjamin, pub. 1965.
March, Advanced Organic Chemistry, Reactions, Mechanisms, and Structure, Second Edition, p. 386, McGraw–Hill, 1979.

*Primary Examiner*—Alan L. Rotman
*Attorney, Agent, or Firm*—Burns, Doane, Swecker & Mathis

[57] ABSTRACT

A 2-pyridylacetic acid derivative having the formula (I):

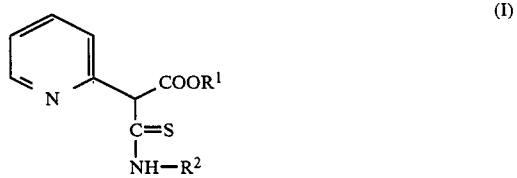

wherein $R^1$ represents an alkyl having 5 to 10 carbon atom or —$(CH_2)_m$—cycloalkyl group having $C_5$-$C_8$ cycloalkyl, which may be substituted with at least one alkyl group having 1 to 6 carbon atoms, where m represents zero or an integer of 1 to 4; $R^2$ represents hydrogen, a linear alkyl, a hydroxyalkyl group, an alkenyl, an aryl, an aralkyl or a group—$(CH_2)$—A, where n represents an integer of 0 to 3 and A represents a nitrogen-containing heterocyclic group which may be replaced by an alkyl having 1 to 10 carbon atoms or an aralkyl having 7 to 10 carbon atoms and a pharmacologically acceptable acid addition salt thereof, which has the effects of both an inhibition of gastric acid and a protection of gastric mucosa, and which has a low toxicity.

3 Claims, No Drawings

2-PYRIDYLACETIC ACID DERIVATIVE, AND PHARMACEUTICAL COMPOSITION CONTAINING THE SAME AND METHOD OF TREATING A PEPTIC ULCER

CROSS-REFERENCE TO RELATED APPLICATION

This application is a continuation-in-part of Ser. No. 925,175, filed Oct. 31, 1986.

BACKGROUND OF THE INVENTION

1. Field of the Invention

The present invention relates to a 2-pyridylacetic acid having the formula (I):

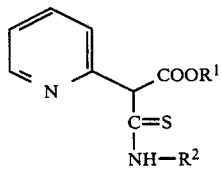

wherein $R^1$ represents an alkyl having 5 to 10 carbon atom or $-(CH_2)_m$-cycloalkyl group having $C_5-C_8$ cycloalkyl, which may be substituted with at least one alkyl group having 1 to 6 carbon atoms, where m represents zero or an integer of 1 to 4; $R^2$ represents hydrogen, a linear alkyl preferably having 1 to 10 carbon atoms, a hydroxyalkyl preferably having 2 to 6 carbon atoms, an alkenyl preferably having 3 to 6 carbon atoms, an aryl preferably having 6 to 10 carbon atoms, an aralkyl preferably having 7 to 15 carbon atoms or a group $-(CH_2)_n-$a, where n represents an integer of 0 to 3 and A represents a nitrogen-containing heterocyclic group which may be substituted with an alkyl having 1 to 10 carbon atoms or an aralkyl having 7 to 10 carbon atoms, a process for preparation thereof and a pharmaceutical composition or agent containing the same. More specifically, the 2-pyridylacetic acid derivatives and its pharmaceutically acceptable acid addition salts are novel compounds useful as therapeutical agents for peptic ulcers, since they have the effect of inhibiting attacking factors of peptic ulcer and the effect of potentiating defending factors and also have a low toxicity.

2. Description of the Related Art

The etiology of peptic ulcer has been discussed in terms of an imbalance between aggressive and defensive factors, but the factors which increase the resistance of tissue have not yet been clarified. Accordingly, the maximum to "no acid, no ulcer" remains still true, and under the present situation, the therapy target of peptic ulcers is still directed to a control of gastric acid.

In the recent years, potent inhibitors of gastric acid secretion such as histamine $H_2$ receptor antagonist (cimetidine, ranitidine, famotidine) and anticholinergics of gastric acid (pirenzepine) were introduced to therapeutics of gastric and duodenal ulcer patients. However, there are not sufficient for preventing a worsening or recurrence of an ulcer.

As mentioned above, a satisfactory effect cannot be obtained in the therapy of an ulcer only by the use of a drug which can prevent the generation of an ulcer, i.e., inhibit aggressive factors. Accordingly, under the present situation, a drug inhibiting aggressive factors and a protective drug for gastric mucosa are respectively selected or used in combinations of both types as the ulcer therapeutical agent, depending on the conditions of the disease. Although some compounds stated to have both such effects have been proposed, in practice these proved to have a weak inhibiting acid secretion, and to primarily have a protective effect for gastric mucosa.

SUMMARY OF THE INVENTION

As described above, the development of a potent anti-peptic ulcer drug well balanced in both the actions of inhibition of aggressive factors and protection of gastric mucosa is strongly desire. Further, it is also important that such a drug should have a very low toxicity and a minimum of side effects as a drug for peptic ulcer disease.

Accordingly, the object of the present invention is to provide a novel compound, in which the above-mentioned activities are well balanced, and having a low toxicity.

Other objects and advantages of the present invention will be apparent from the following description.

In accordance with the present invention, there is provided 2-pyridylacetic acid derivatives having the above-mentioned formula (I) a pharmacologically acceptable acid addition salt thereof.

In accordance with the present invention, there is also provided a process for preparing the compound having the formula (I) and a pharmacologically acceptable acid addition salt thereof which comprises reacting an addition product having the formula (III):

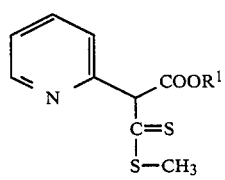

wherein $R^1$ is as defined above; with ammonia or an amine represented by the formula (IV):

wherein $R^2$ is as defined above, followed by treatment with a pharmaceutically acceptable acid, if desired.

In accordance with the present invention, there is also provided a peptic ulcer therapeutical agent comprising the 2-pyridylacetic acid derivative having the formula (I) and/or a pharmacologically acceptable acid addition salt thereof as the active ingredient.

DESCRIPTION OF THE PREFERRED EMBODIMENTS

The novel compound 2-pyridylacetic acid derivative having the above-mentioned formula (I) and its pharmacologically acceptable acid addition salt according to the present invention has a protecting action of gastric mucosa together with an effect of inhibiting gastric acid secretion, and has a low toxicity, and therefore, is a useful substance which can be used for the therapy of a peptic ulcer.

The compound having the above-mentioned formula (I) of the present invention can be prepared as follows:

That is, a 2-pyridylacetic acid ester having the formula (II):

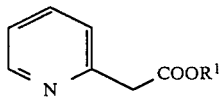

wherein $R^1$ is as defined above, is allowed to react with carbon disulfide in an organic solvent in the presence of a base at a temperature of −78° C. to 0° C. The reaction is completed within several minutes to several tens of minutes. After completion of the reaction, methyl iodide is added and stirring is continued for several hours, whereby an addition product having the formula (III):

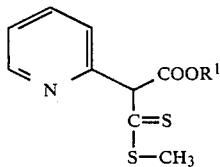

wherein $R^1$ is as defined above, can be obtained.

The solvent usable in the above reaction, may include, for example, an ether such as tetrahydrofuran, diethyl ether, dimethoxyethane or dioxane, or an aromatic hydrocarbon such as benzene, toluene or xylene, or dimethyl sulfoxide. Alternatively, the base usable in the above reaction may preferably include an alkyl lithium reagent, sodium amide, sodium hydride, potassium hydride, potassium t-butoxide, a sodium alcoholate, a potassium alcoholate, metallic sodium, and the like.

The amount of the base to be used in the above-mentioned reaction is not particularly limited, but may be, for example, 1,2 equivalent relative to the above compound (II).

The thus-obtained addition product having the formula (III) can be purified by any conventional purification method, for example, chromatography, recrystallization or distillation.

When the above compound (III) is allowed to react with ammonia or an amine having the formula (IV):

$$R^2-NH_2 \quad \text{(IV)}$$

wherein $R^2$ is as defined above, in water and an organic solvent, or in an organic solvent, for 1 to 10 hours, the present compound can be obtained. The solvent usable in this reaction is not particularly limited, unless the reaction is adversely affected, but preferably, for example, water, an alcoholic solvent, a chlorine type solvent, a aromatic hydrocarbon solvent, an ether solvent, or an acetic acid ester solvent is used.

After completion of the reaction, the desired compound can be purified by, for example, recrystallization, column chromatography, or alternatively it can be treated with a pharmacologically acceptable acid and converted into an acid addition salt, which, in turn, can be purified by recrystallization or chromatography.

The acids usable for the preparation of the acid addition salts of the above 2-pyridylacetic acid derivative according to the present invention may include, for example, inorganic acids such as hydrochloric acid, hydrobromic acid, sulfuric acid, phosphoric acid, perchoric acid, and the like, and organic acids such as acetic acid, oxalic acid, citric acid, lactic acid, maleic acid, succinic acid, fumaric acid, tartaric acid, gluconic acid, mandelic acid, methanesulfonic acid, and the like.

Another process for preparing the 2-pyridylacetic acid derivative according to the present invention comprises dissolving a compound having the above formula (II) in an organic solvent and treating it with a base at a temperature of 0° C. or lower. Examples of such organic solvents are, preferably, ether solvents and aromatic hydrocarbon solvents. The amount of the base used in the above reaction is not particularly limited, but is preferably used at 1.0 to 1.2 equivalent relative to the compound of the above formula (II). Examples of such bases are, preferably, sodium hydride, a sodium alkoxide, a potassium alkoxide, sodium amide, n-butyllithium, and metallic sodium.

In the next step, an isothiocyanate having the formula (V):

$$S=C=N-R^3 \quad \text{(V)}$$

wherein $R^3$ represents a linear or straight chain or cyclic alkyl group, an alkenyl group, an aryl group or an aaralkyl group, is added to the above-mentioned reaction mixture, whereby a compound according to the present invention having the formula (Ia):

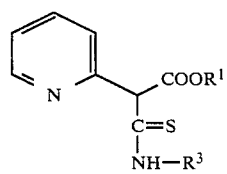

wherein $R^1$ and $R^3$ are as defined above, can be obtained.

The novel 2-pyridylacetic acid having the above formula (I) according to the present invention may be administered as it is, but can be formed in various kinds of dosage forms by utilizing known preparation methods. For example, for oral administration, it can be generally formed into preparations such as tablets, powders, granules, capsules, syrup, and the like, or for parenteral administration, can be injected or filled in suppositories, and the like. In either case, preparations with various forms can be obtained by mixing with known liquid or solid excipients or carriers conventionally used in the preparation.

Examples of such excipients or carriers may include polyvinyl pyrrolidone, gum arabic, gelatin, sorbitol, tragacanth, magnesium stearate, talc, polyethylene glycol, polyvinyl alcohol, silica, lactose, crystalline cellulose, sugar, starch, calcium phosphate, vegetable oil, carboxymethyl cellulose calcium, sodium lauryl sulfate, water, ethanol, glycerine, mannitol, syrup, and the like.

The peptic ulcer therapeutical agent of the present invention can contain the compound having the formula (I), or a pharmacologically acceptable acid addition salt thereof, in an effective amount.

The effective amount of the peptic ulcer therapeutical agent of the present invention to be administered may be varied depending on the condition and the age of the patient to be treated, the administration route, the dosage form, the number of administrations, and the like, but may be, for example, generally within the scope of from about 5 to 1,000 mg, preferably from 10 to 500 mg, for a human adult per day.

EXAMPLES

The present invention will now be further illustrated by, but is by no means limited to, the following Examples.

The compounds having the above formula (I) of the present invention were synthesized according to the two methods as described below. The method incorporating the formula (III) is called method B, and the method for obtaining the compound (Ia) of the present invention by allowing an isothiocyanate to react directly with the formula (II) is called method A.

EXAMPLE 1

Synthesis of iso-amyl-2-(2-pyridyl)acetate

A mixture of 2-pyridylacetic acid hydrochloride 10.00 g (57.60 mmol), iso-amyl alcohol 6.09 g (69.12 mmol) and 1-ethyl-3-(3-dimethylaminopropyl)carbodiimide hydrochloride 14.35 g (74.88 mmol) in 20 ml of pyridine and 80 ml of methylene chloride was stirred at room temperature for 2 hr.

The reaction mixture was quenched with 200 ml of water, and extracted with chloroform. The extract was washed with water and dried over anhydrous magnesium sulfate. The residue obtained by evaporation of the solvent was distilled to give 9.72 g of the desired compund as an yellow oil.

The various compounds listed in Table 1 were prepared in the same manner as in Example 1. The physical properties of these starting compounds are also summarized in Table 1.

TABLE 1 pyridyl-CH$_2$-COO-R$^1$

| No. | R$^1$ | b.p. | IR $\nu$ cm$^{-1}$ | NMR(CDCl$_3$)$\sigma$: | Yield % |
|---|---|---|---|---|---|
| 1 | isoamyl (CH$_3$)$_2$CHCH$_2$CH$_2$– | yellow oil b.p.$_{1.2}$ 104–105° | 2950, 1730, 1588, 1465, 1430, 1250, 1150, 890, 740 (NaCl) | 0.89 (6H, d, J = 6.6 Hz), 1.45–1.75 (3H, m), 3.84 (2H, s), 4.16 (2H, t, J = 6.6 Hz), 7.19 (1H, m), 7.29 (1H, d, J = 7.9 Hz), 7.66 (1H, m), 8.55 (1H, d, J = 5.3 Hz) | 81 |
| 2 | (CH$_3$)$_2$CHCH$_2$CH$_2$CH(CH$_3$)– | yellow oil b.p.$_1$ 142–143° | 2940, 1735, 1585, 1460, 1250, 1150, 990, 740 (NaCl) | 0.86 (9H, d, J = 6.6 Hz), 1.06–1.70 (10H, m), 3.84 (2H, s), 4.16 (2H, m), 7.18 (1H, m), 7.29 (1H, d, J = 7.9 Hz), 7.65 (1H, m), 8.55 (1H, d, J = 4.6 Hz) | 74 |
| 3 | CH$_3$CH$_2$C(CH$_3$)$_2$CH$_2$– (neopentyl-type) | yellow oil b.p.$_{0.4}$ 88–91° | 2950, 1730, 1590, 1480, 1435, 1370, 1250, 1150, 1000, 750 (NaCl) | 0.88 (9H, s), 3.81 (2H, s), 3.88 (2H, s), 7.20 (1H, m), 7.31 (1H, d, J = 7.9 Hz), 7.65 (1H, m), 8.56 (1H, d, J = 5.6 Hz) | 86 |
| 4 | cyclopentylmethyl (5H ring)–CH$_2$– | yellow oil b.p.$_{1.2}$ 120° | 2950, 2860, 1730, 1590, 1470, 1430, 1250, 1155, 990, 745 (NaCl) | 1.05–1.80 (8H, m), 2.19 (1H, m), 3.85 (2H, s), 4.01 (2H, d, J = 6.6 Hz), 7.19 (1H, m), 7.30 (1H, d, J = 7.9 Hz), 7.65 (1H, m), 8.56 (1H, d, J = 4.6 Hz) | 72 |
| 5 | cyclohexyl (6H ring)– | yellow oil b.p.$_{1.2}$ 117–119° | 2940, 2850, 1730, 1590, 1430, 1250, 1160, 1005, 965, 750 (NaCl) | 1.17–1.85 (10H, m), 3.85 (2H, s), 4.81 (1H, m), 7.20 (1H, m), 7.32 (1H, d, J = 7.9 Hz), 7.67 (1H, m), 8.56 (1H, d, J = 4.6 Hz) | 74 |
| 6 | cyclohexylmethyl (6H ring)–CH$_2$– | yellow oil b.p.$_1$ 140–142° | 2920, 2850, 1730, 1590, 1430, 1250, 1150, 990, 740 (NaCl) | 0.82–1.75 (11H, m), 3.86 (2H, s), 3.93 (2H, 6.6 Hz), 7.20 (1H, m), 7.30 (1H, d, J = 7.9 Hz), 7.66 (1H, m), 8.56 (1H, d, J = 4.6 Hz) | 85 |
| 7 | 4-ethylcyclohexyl-CH$_2$– (6H ring with CH$_3$) | yellow oil b.p.$_{1.5}$ 163° | 2920, 2840, 1730, 1590, 1430, 1330, 1250, 1150, 990, 740 (NaCl) | 0.76–1.76 (17H, m), 3.88 (2H, s), 3.94 (2H, d, J = 6.6 Hz), 7.21 (1H, m), 7.32 (1H, d, J = 7.9 Hz), 7.69 (1H, m), 8.57 (1H, d, J = 5.9 Hz) | 75 |
| 8 | 4-propylcyclohexyl-CH$_2$– (6H ring with CH$_2$CH$_3$) | yellow oil b.p.$_{1.5}$ 169° | 2900, 2840, 1730, 1580, 1330, 1250, 1150, 990, 740 (NaCl) | 0.79–1.80 (19H, m), 3.88 (2H, s), 3.94 (2H, d, J = 6.6 Hz), 7.21 (1H, m), 7.33 (1H, d, J = 7.9 Hz), 7.69 (1H, m), 8.56 (1H, d, J = 7.9 Hz) | 74 |
| 9 | 4-butylcyclohexyl-CH$_2$– (6H ring with longer alkyl-CH$_3$) | yellow oil b.p.$_{1.5}$ 179° | 2930, 2850, 1740, 1590, 1440, 1340, 1250, 1150, 740 (NaCl) | 0.76–1.82 (21H, m), 3.89 (2H, s), 3.94 (2H, d, J = 5.9 Hz), 7.23 (1H, m), 7.33 (1H, d, J = 7.9 Hz), 7.70 (1H, m), 8.57 (1H, d, J = 4.6 Hz) | 74 |

TABLE 1-continued

[Structure: pyridine-CH2-COO-R¹]

| No. | R¹ | b.p. | IR ν cm⁻¹ | NMR(CDCl₃)σ: | Yield % |
|-----|----|----|----|----|----|
| 10 | (cyclohexyl-propyl, 6H) | yellow oil b.p.₁.₃ 155–157° | 2920, 2840, 1730, 1580, 1250, 1150, 990, 740 (NaCl) | 0.82–1.72 (13H, m), 3.85 (2H, s), 4.16 (2H, t, J = 7.3 Hz), 7.17–7.31 (2H, m), 7.67 (1H, m), 8.56 (1H, d, J = 3.9 Hz) | 74 |
| 11 | (cyclohexyl-butyl, 6H) | yellow oil b.p.₀.₅ 151° | 2920, 2850, 1740, 1590, 1440, 1335, 1250, 1150, 745 (NaCl) | 0.82–1.75 (15H, m), 3.84 (2H, s), 4.09 (2H, t, J = 7.3 Hz), 7.18 (1H, m), 7.29 (1H, d, J = 7.9 Hz), 7.65 (1H, m), 8.56 (1H, d, J = 4.0 Hz) | 84 |
| 12 | (cyclohexyl-pentyl, 6H) | yellow oil b.p.₁.₅ 165° | 2920, 2850, 1740, 1590, 1450, 1335, 1250, 1050, 740 (NaCl) | 0.75–1.70 (17H, m), 3.84 (2H, s), 4.11 (2H, t, J = 6.6 Hz), 7.18 (1H, m), 7.29 (1H, d, J = 7.9 Hz), 7.65 (1H, t, d, J = 7.9 Hz, J = 2.0 Hz), 8.55 (1H, d, J = 4.0 Hz) | 81 |
| 13 | (cycloheptyl-methyl, 7H) | yellow oil b.p.₁.₂ 144–148° | 2920, 2860, 1740, 1595, 1470, 1440, 1260, 1160, 1000, 750 (NaCl) | 1.10–1.87 (13H, m), 3.85 (2H, s), 3.92 (2H, d, J = 6.6 Hz), 7.19 (1H, m), 7.30 (1H, d, J = 7.9 Hz), 7.65 (1H, m), 8.56 (1H, d, J = 4.6 Hz) | 78 |

EXAMPLE 2-A

Synthesis of iso-amyl-2-methylthiocarbamoyl-2-(2-pyridyl)acetate hydrochloride (Synthesis according to method A)

A 2.0 g (9.6 mmol) amount of iso-amyl 2-pyridylacetamte was dissolved in 20 ml of dry tetrahydrofuran, and to the resultant solution were added, under a nitrogen gas stream and at a temperature of −78° C. to 0° C., 1.1 equivalent of n-butyl lithium solution in hexane or 1.1 equivalent or powdery sodium amide, followed by stirring for 15 to 30 minutes.

To the resultant solution was added 0.78 g (10.6 mmol) of methylisothiocyanate, and the mixture was stirred at room temperature for 2 hours. Water was then added to the reaction mixture, and the mixture was extracted with chloroform. The organic layer was then washed with water, and dried over anhydrous magnesium sulfate.

The residue obtained by evaporation of the solvent was subjected to column chromatography on silica gel to obtain an yellow oil, which was converted to 2.41 g of the HCl salt (yield 79%).

EXAMPLE 2-B

Synthesis of iso-amyl-2-methylthiocarbamoyl-2-(2-pyridyl)acetate hydrochloride (Synthesis according to method B)

A 3.00 g (14.5 mmol) amount of iso-amyl 2-pyridylacetate was dissolved in 30 ml of dry tetrahydrofuran, and to the resultant solution was added, under a nitrogen stream at −78° C., 1.1 equivalent of n-butyl lithium solution in hexane. After 15 minutes, 1.21 g (15.9 mmol) of carbon disulfide was added, and further, after stirring for 15 minutes, 2.16 g (15.9 mmol) of methyl iodide was added, followed by stirring for 2 hours.

Water was added to the reaction mixture obtained above, and the mixture was extracted with chlorform.

The organic layer was then washed with water, followed by drying over anhydrous magnesium sulfate.

The residue obtained by evaporation of the solvent was subjected to column chromatography on silica gel to obtain iso-amyl 2-dithiomethoxycarbonyl-2-(2-pyridyl)acetate as an yellow oil (yield 81%).

The resultant product was dissolved in 30 ml of dioxane and excess ammonia gas was bubbled into the above solution for 20 min. at room temperature, and the mixture was further stirred for 5 hours. The residue obtained by concentration was subjected to column chromatography on silica gel to obtain an oil, which was converted to 1.15 g of the HCl salt (yield 26%).

The various compounds listed in Table 2 were prepared in the same manner as in Example 2. The physical properties of these compounds are summarized in Table 2.

The compounds thus obtained are as follows:

1. iso-Amyl 2-(2-pyridyl)-2-thiocarbamoylacetate hydrochloride
2. iso-Amyl 2-methylthiocarbamoyl-2-(2-pyridyl)-acetate hydrochloride
3. 3,7-Dimethyloctyl-2-(2-pyridyl)-2-thiocarbamoylacetate hydrochloride
4, 3,7-Dimethyloctyl methylthiocarbamoyl-2-(2-pyridyl)acetate hydrochloride
5. 2,2-Dimethylpropyl 2-(2-pyridyl)-2-thiocarbamoylacetate hydrochloride
6. 2,2-Dimethylpropyl 2-methylthiocarbamoyl-2-(2-pyridyl)acetate hydrochloride
7. Cyclopentylmethyl 2-(2-pyridyl)-2-thiocarbamoylacetate hydrochloride
8. Cyclopentylmethyl 2-methylthiocarbamoyl-2-(2-pyridyl)acetate
9. Cyclohexyl 2-(2-pyridyl)-2-thiocarbamoyl-acetate hydrochloride
10. Cyclohexyl 2-methylthiocarbamoyl-2-(2-pyridyl)acetate
11. Cyclohexylmethyl 2-(2-pyridyl)-2-thiocarbamoylacetate hydrochloride 12. Cyclohexylmethyl 2-methylthiocarbamoyl-2-(2-pyridyl)acetate hydrochloride
13. (trans-4-n-Propylcyclohexyl)methyl 2-(2-pyridyl)-2-thiocarbamoylacetate hydrochloride
14. (trans-4-n-Propylcyclohexyl)methyl 2-methylthiocarbamoyl-2-(2-pyridyl)acetate hydrochloride
15. (trans-4-n-Butylcyclohexyl)methyl 2-(2-pyridyl)-2-thiocarbamoylacetate hydrochloride
16. (trans-4-n-Butylcyclohexyl)methyl 2-methylthiocarbamoyl-2-(2-pyridyl)acetate hydrochloride
17. (trans-4-n-Pentylcyclohexyl)methyl 2-(2-pyridyl)-2-thiocarbamoylacetate hydrochloride
18. (trans-4-n-Pentylcyclohexyl)methyl 2-methylthiocarbamoyl-2-(2-pyridyl)acetate hydrochloride
19. Cyclohexylethyl 2-(2-pyridyl)-thiocarbamoylacetate hydrochloride
20. Cyclohexylethyl 2-methylthiocarbamoyl-2-(2-pyridyl)acetate hydrochloride
21. Cyclohexylpropyl 2-(2-pyridyl)-2-thiocarbamoylacetate hydrochloride
22. Cyclohexylpropyl 2-methylthiocarbamoyl-2-(2-pyridyl)acetate hydrochloride
23. Cyclohexylbutyl 2-(2-pyridyl)-2-thiocarbamoylacetate hydrochloride
24. Cyclohexylbutyl 2-methylthiocarbamoyl-2-(2-pyridyl)acetate hydrochloride
25. Cycloheptylmethyl 2-(2-pyridyl)-2-thiocarbamoylacetate hydrochloride
26. Cycloheptylmethyl 2-methylthiocarbamoyl-2-(2-pyridyl)acetate

TABLE 2

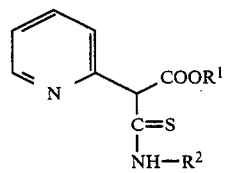

| No. | $R^1$ | $R^2$ | mp °C. | IR $\nu cm^{-1}$ | NMR(CDCl$_3$)$\sigma$: | method & yield (%) |
|---|---|---|---|---|---|---|
| 1 | isobutyl (CH(CH$_3$)CH$_2$—, with CH$_3$) | H | colorless prisms HCl salt 96–104 | 3280, 3100, 2950, 2650, 1750, 1630, 1450, 1300, 1180, 1000, 750 (KBr) | 0.93(6H, d, J=6.6Hz), 1.50–1.85(3H, m), 4.26(2H, m), 6.65(1H, s), 7.62(1H, br.s), 7.89(1H, m), 8.45(1H, m), 8.58(1H, d, J=4.6Hz), 8.75(1H, d, J=7.9Hz), 10.01(1H, br.s) | B 26 |
| 2 | isobutyl | CH$_3$ | colorless prisms HCl salt 72–77 | 3400, 3180, 2950, 1740, 1460, 1380, 1250, 750 (KBr) | 0.92(6H, d, J=6.6Hz), 1.50–1.80(3H, m), 3.12(3H, d, J=4.6Hz), 4.25(2H, m), 6.63 (1H, s), 7.83(1H, m), 8.43(1H, m), 8.44(1H, s), 7.83(1H, m), 8.43(1H, m), 8.44(1H, d, J=4.6Hz), 8.78(1H, d, J=7.9Hz), 10.51(1H, br.s) | A 79 |
| 3 | 2,6-dimethylheptyl | H | colorless prisms HCl salt 99–116 | 3280, 2960, 2700, 1750, 1630, 1450, 1290, 1180, 985, 750 (KBr) | 0.87(6H, d, J=6.6Hz), 0.91(3H, d, J=6.6Hz), 1.05–1.80(10H, m), 4.28(2H, m), 6.65(1H, s), 7.57(1H, br.s), 7.89(1H, m), 8.45(1h, m), 8.56(1H, d, J=5.9Hz), 8.75 (1H, d, J=8.6Hz), 10.01(1H, br.s) | B 36 |
| 4 | 2,6-dimethylheptyl | CH$_3$ | HCl salt colorless powder | 3400, 3180, 2950, 2640, 1730, 1540, 1460, 1380, 760 (KBr) | 0.87(6H, d, J=5.9Hz), 0.89(3H, d, J=6.6Hz), 1.05–1.80(10H, m), 3.12(3H, d, J=4.6Hz), 4.25(2H, m), 6.62(1H, s), 7.86(1H, m), 8.42(1H, t, J=7.9Hz), 8.54(1H, d, J=5.3Hz), 8.77(1H, d, J=7.9Hz), 10.50(1H, br.s) | A 93 |
| 5 | neopentyl (C(CH$_3$)$_3$CH$_2$—) | H | HCl salt colorless prisms 112–117 | 3300, 2950, 2600, 1750, 1630, 1445, 1370, 1300, 1230, 1180, 1005, 740 (KBr) | 0.98(9H, s), 3.80(1H, d, J=10.1Hz), 4.05 (1H, d, J=10.1Hz), 6.67(1H, s), 7.65(1H, br.s), 7.90(1H, m), 8.45(1H, m), 8.58(1H, d, J=5.3Hz), 8.72(1H, d, J=7.9Hz), 9.99(1H, br.s) | B 73 |
| 6 | neopentyl | CH$_3$ | HCl salt colorless prisms 115–120 | 3150, 2950, 1730, 1600, 1480, 1390, 1165, 1070, 990, 800, 750 (KBr) | 0.95(9H, s), 3.14(3H, d, J=4.0Hz), 3.63 (1H, d, J=4.6Hz), 3.91(1H, d, J=4.6Hz), 6.65(1H, s), 7.87(1H, m), 8.43(1H, m), 8.53 (1H, d, J=5.3Hz), 8.76(1H, d, J=8.6Hz) | A 68 |
| 7 | cyclopentylmethyl | H | colorless prisms HCl salt 114–116 | 3300, 2950, 1750, 1630, 1450, 1300, 1180, 750 (KBr) | 1.21–1.86(8$^{11}$, m), 2.27(1H, m), 4.12(2H, m), 6.63(1H, s), 7.59(1H, br.s), 7.89(1H, m), 8.45(1H, m), 8.56(1H, d, J=5.3Hz), 8.73 (1H, d, J=7.9Hz), 10.00(1H, br.s) | B 46 |
| 8 | cyclopentylmethyl | CH$_3$ | colorless prisms 62–64 | 3150, 2950, 1750, 1570, 1480, 1380, 1160, 750 (KBr) | 1.08–1.17(2H, m), 1.45–1.67(6H, m), 2.13 (1H, m), 3.23(3H, d, J=5.3Hz), 4.00(2H, m), 5.41(1H, s), 7.29(1H, d.d, J=4.6Hz, 1.3Hz), 7.44(1H, d, J=7.3Hz), 7.73(1H, t.d, J=7.3Hz, J=1.3Hz), 8.56(1H, d, J=4.6Hz), 10.24(1H, br.s) | A 51 |

TABLE 2-continued

Structure: pyridine-CH(COOR¹)-C(=S)-NH-R²

| No. | R¹ | R² | mp °C. | IR νcm⁻¹ | NMR(CDCl₃)σ: | method & yield (%) |
|---|---|---|---|---|---|---|
| 9 | cyclohexyl | H | HCl salt colorless prisms 134–145 | 3270, 2930, 2600, 1750, 1630, 1445, 1290, 1180, 1005, 750 (KBr) | 1.20–2.00(10H, m), 4.91(1H, m), 6.58(1H, s), 7.64(1H, br.s), 7.89(1H, m), 8.45(1H, m), 8.59(1H, d, J=5.9Hz), 8.75(1H, d, J=7.9Hz), 9.98(1H, br.s) | B 37 |
| 10 | cyclohexyl | CH₃ | colorless prisms 85–86 | 3170, 2930, 1750, 1565, 1475, 1290, 1170, 750 (KBr) | 1.16–1.86(10H, m), 3.22(3H, d, J=5.3Hz), 4.81(1H, m), 5.47(1H, s), 7.31(1H, m), 7.55 (1H, d, J=7.9Hz), 7.77(1H, m), 8.55(1H, d, J=4.6Hz), 10.26(1H, br.s) | A 33 |
| 11 | cyclohexyl-CH₂ | H | colorless prisms HCl salt 135–144 | 3050, 2930, 1730, 1625, 1460, 1440, 1180, 1005, 770, 750 | 0.90–1.33(5H, m), 1.66–1.84(6H, m), 3.94–4.13(2H, m), 6.61(1H, s), 7.80(1H, br.s), 7.89 (1H, br.t, J=6.6Hz), 8.44(1H, br.t, J=7.9Hz), 8.63(1H, d, J=5.3Hz), 8.73(1H, d, J=8.8Hz), 10.0(1H, br.s) | B 64 |
| 12 | cyclohexyl-CH₂ | CH₃ | colorless prisms HCl salt 131–139 | 3400, 3160, 2920, 1730, 1610, 1530, 1480, 1390, 1170, 1080, 750 (KBr) | 0.89–1.81(11H, m), 3.13(3H, d, J=4.6Hz), 4.05(2H, m), 6.63(1H, s), 7.86(1H, m), 8.41 (1H, m), 8.52(1H, m), 8.78(1H, d, J=8.6Hz), 10.50(1H, br.s) | A 72 |
| 13 | 4-methylcyclohexyl-CH₂ | H | HCl salt colorless prisms 138–144 | 3360, 2920, 2600, 1740, 1630, 1545, 1450, 1300, 1190, 950, 760 (KBr) | 0.82–1.87(17H, m), 4.04(2H, m), 6.65(1H, s), 7.62(1H, br.s), 7.90(1H, m), 8.45(1H, t.d, J=7.9Hz, J=1.3Hz), 8.57(1H, d, J=5.9Hz), 8.74(1H, d, J=7.9Hz), 10.01(1H, br.s) | B 53 |
| 14 | 4-methylcyclohexyl-CH₂ | CH₃ | HCl salt colorless prisms 117–122 | 3150, 2920, 2550, 1550, 1460, 1380, 1290, 1210, 1170, 740 (KBr) | 0.77–1.83(17H, m), 3.13(3H, d, J=5.3Hz), 4.03(2H, m), 6.64(1H, s), 7.82(1H, m), 8.43 (1H, m), 8.54(1H, d, J=5.9Hz), 8.78(1H, d, J=8.5Hz), 10.50(1H, br.s) | A 51 |
| 15 | 4-methylcyclohexyl-CH₂CH₂ | H | HCl salt colorless prisms 136–143 | 3270, 2920, 2600, 1745, 1630, 1550, 1450, 1300, 1185, 1000, 760 (KBr) | 1.75–1.80(19H, m), 4.04(2H, m), 6.64(1H, s), 7.70(1H, br.s), 7.90(1H, m), 8.46(1H, m), 8.60(1H, d, J=5.3Hz), 8.74(1H, d, J=8.6Hz), 10.00(1H, br.s) | B 58 |
| 16 | 4-methylcyclohexyl-CH₂CH₂ | CH₃ | HCl salt colorless prisms 116–121 | 3160, 2920, 2600, 1740, 1550, 1470, 1390, 1210, 740 (KBr) | 0.79–1.84(19H, m), 3.13(3H, d, J=4.6Hz), 4.02(2H, m), 6.63(1H, s), 7.89(1H, m), 8.45 (1H, m), 8.58(1H, d, J=5.3Hz), 8.78(1H, d, J=8.6Hz), 10.53(1H, br.s) | A 74 |
| 17 | 4-methylcyclohexyl-(CH₂)₃ | H | HCl salt colorless prisms 144–148 | 3270, 2930, 2600, 1740, 1630, 1450, 1300, 1190, 760 (KBr) | 0.82–1.85(21H, m), 4.03(2H, m), 6.65(1H, s), 7.63(1H, br.s), 7.90(1H, m), 8.45(1H, t.d, J=7.9Hz), J=1.3Hz), 8.58(1H, d, J=5.9Hz), 8.74(1H, d, J=7.9Hz), 10.01(1H, br.s) | B 70 |
| 18 | 4-methylcyclohexyl-(CH₂)₃ | CH₃ | HCl salt colorless prisms 121–122 | 3150, 2920, 2600, 1740, 1550, 1470, 1390, 1210, 740 (KBr) | 0.85–1.85(21H, m), 3.13(3H, d, J=5.3Hz), 4.02(2H, m), 6.64(1H, s), 7.87(1H, m), 8.43 (1H, m), 8.53(1H, d, J=5.3Hz), 8.78(1H, d, J=8.6Hz), 10.50(1H, br.s) | A 91 |
| 19 | propylcyclohexyl (isomer) | H | HCl salt colorless prisms 127–138 | 3250, 2920, 2600, 1750, 1620, 1440, 1290, 1170, 980, 745 (KBr) | 0.86–1.73(13H, m), 4.15–4.39(2H, m), 6.63 (1H, s), 7.70(1H, br.s), 7.90(1H, t, J=6.6Hz), 8.46(1H, t, J=7.9Hz), 8.60(1H, d, J=5.3Hz), 8.74(1H, d, J=7.9Hz), 10.00 (1H, br.s) | B 63 |
| 20 | propylcyclohexyl (isomer) | CH₃ | HCl salt colorless prisms 78–82 | 3400, 3160, 2930, 1740, 1470, 1390, 1260, 1180, 750 (KBr) | 0.85–1.80(13H, m), 3.13(3H, d, J=4.6Hz), 4.25(2H, m), 6.63(1H, s), 7.85(1H, m), 8.42 (1H, t.d, J=7.9Hz, J=2.0Hz), 8.52(1H, d, J=5.9Hz), 8.78(1H, d, J=7.9Hz), 10.50 (1H, br.s) | A 70 |

TABLE 2-continued

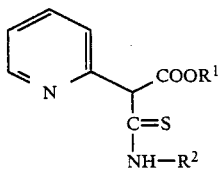

| No. | R¹ | R² | mp °C. | IR νcm⁻¹ | NMR(CDCl₃)σ: | method & yield (%) |
|---|---|---|---|---|---|---|
| 21 | ~~~⟨6H⟩ | H | HCl salt colorless prisms 99–105 | 3260, 2920, 2840, 2600, 1740, 1630, 1440, 1180, 990, 740 (KBr) | 0.83–1.72(15H, m), 4.21(2H, m), 6.65(1H, s), 7.62(1H, br.s), 7.90(1H, br.s), 8.46(1H, m), 8.58(1H, br.s), 8.75(1H, d, J=7.9Hz), 10.01(1H, br.s) | B 36 |
| 22 | ~~~⟨6H⟩ | CH₃ | HCl salt colorless prisms 77–83 | 3150, 2920, 2600, 1740, 1550, 1470, 1380, 1210, 1170, 990, 745 (KBr) | 0.84–1.71(15H, m), 3.13(3H, d, J=4.6Hz), 4.20(2H, m), 6.63(1H, s), 7.87(1H, m), 8.43 (1H, m), 8.53(1H, d, J=5.3Hz), 8.78(1H, d, J=7.9Hz), 10.51(1H, br.s) | A 87 |
| 23 | ~~~~⟨6H⟩ | H | HCl salt colorless prisms 135–137 | 3300, 2920, 2600, 1745, 1630, 1450, 1300, 1230, 1170, 1000, 750 (KBr) | 0.80–1.77(17H, m), 4.23(2H, m), 6.65(1H, s), 7.60(1H, br.s), 7.90(1H, t, J=7.3Hz), 8.46(1H, m), 8.57(1H, d, J=5.3Hz), 8.75 (1H, d, J=8.6Hz), 10.02(1H, br.s) | B 71 |
| 24 | ~~~~⟨6H⟩ | CH₃ | HCl salt colorless prisms 105–108 | 3300, 3150, 2920, 2600, 1740, 1550, 1470, 1385, 1210, 745 (KBr) | 0.80–1.76(17H, m), 3.13(3H, d, J=4.6Hz), 4.21(2H, m), 6.63(1H, s), 7.87(1H, m), 8.43 (1H, m), 8.54(1H, d, J=5.3Hz), 8.78(1H, d, J=7.9Hz), 10.52(1H, br.s) | A 70 |
| 25 | ~⟨7H⟩ | H | colorless prisms HCl salt 118–122 | 3300, 2930, 2600, 1730, 1620, 1460, 1225, 1180, 1005, 760 (KBr) | 1.10–2.00(13H, m), 4.05(2H, m), 6.63(1H, s), 7.60(1H, br.s), 7.91(1H, m), 8.43(1H, m), 8.56(1H, d, J=4.7Hz), 8.72(7.9Hz), 10.01 (1H, br.s) | B 52 |
| 26 | ~⟨7H⟩ | CH₃ | colorless prisms 55–56 | 3160, 2920, 1750, 1565, 1480, 1385, 1290, 1165, 745 | 1.05–1.78(12H, m), 3.23(3H, d, J=4.6Hz), 3.90(2H, m), 5.40(1H, s), 7.28(1H, m), 7.44 (1H, d, J=7.9Hz), 7.72(1H, m) 8.55(1H, d, J=4.6Hz), 10.23(1H, br.s) | A 83 |

EVALUATION EXAMPLE

| Formulated components | Parts by weight |
|---|---|
| Compound of Example | 95 |
| Lactose | 25 |
| Crystalline cellulose | 10 |
| Corn starch | 100 |

The above components were formulated into preparations according to a conventional method.

For the pharmacological examination of the compounds of the present invention, the following tests were carried out to evaluate the activities of the present compounds.

1. Action on hydrochloride acid plus ethanol induced ulcer

Sprague-Dawley strain male rats weighing 200–240 g were used after starving for 24 hours. To each rat, 60% ethanolic solution containing 150 mM of hydrochloric acid was administered orally at a volume of 0.5 ml/100 g-body weight, and the stomach was removed under ether anesthesia 1 hour later. Into the stomach, 10 ml of a 2% formalin solution was injected, and further the stomach was then immersed in a 2% formalin solution for 15 minutes to fix the inner and outer wall of the stomach. The stomach was cut open along the greater curvature, and the length of the damage generated at the glandular portion of the stomach was measured, and the sum of the lengths of the damages of gastric mucosa per one rat was defined as the lesion index (mm), which was compared with a control group to calculate the percentage of inhibition according to the formula shown below, and then the percentage of inhibition versus dose (mg/kg) was plotted on semi-logarithmic graph to determine the $ED_{50}$ value. Each test drug was suspended in physiological saline a few drops of Tween 80 and administered orally 30 minutes before administration of the hydrochloric acid ethanolic solution.

$$\text{Inhibition (\%)} = \frac{\text{Average lesion index of control group} - \text{Average lesion index of group administered with test compound}}{\text{Average lesion index of control group}} \times 100$$

The results of antisecretory effects of gastric acid and protective effects of the gastric muscosa against HCl-EtOH are as shown in Table 3.

2. Ghosh & Schild rats (methods)

Male Sprague-Dawley rats (200–250 g) were deprived of food but allowed free access to water for 24 hrs. The animals were used under urethane anesthesia (1.25 g/kg, i.p.). The stomach was exposed through a midline incision and a polyethylene cannula was positioned in the forestomach. Another cannula was inserted into the stomach through the duodenum and held in place by a ligature around the pylorus, care being taken not to include blood vessels or bile and pancreatic ducts within the ligature. The stomach was perfused with physiological saline solution at a flow rate of 1 ml/min using a peristalic pump. Both entry and exit tubes, which were connected to the cannula attached to the forestomach and to the pylorus, were positioned in a reservoir in which a pH glass electrode was placed. The titration was performed at luminal pH 7.0 using a pH-stat method (comtite-8, Hiranuma) and by adding 0.1N NaOH to the reservoir under 100% $O_2$ atmosphere. The acid output was continuously monitored on a recorder, Histamine.2HCl (5 mg/kg/h) was continuously perfused into the tail vein at the rate of 2.2 ml/h. After stabilization of the stimulated acid secretion (90mm-2 hr), test samples suspended in the 0.5% CMC or Tween 80-saline were given intraduodenally. The acid output was expressed as $\mu$Eq/30 mm before and 90-120 mm after administration of the drug (30 mg/kg i.d.) during the maximally stimulated acid secretion, and the drug suppression of acid secretion was taken as a percentage of mean acid output before administration of the drug.

The data was analysed with the so-called paired student t test.

3. Anti stress ulcer

Sprague-Dawley-strain male rats weighing about 240-260 g were starved for 24 hours, and 30 minutes after oral administration of the test drug, each rat was placed in a stress cage and stress was loaded by immersing each rat into a water tank maintained at 23° C. to the xiphisternum of the chest. Five hours later, the stomach was removed under ether anesthesia, the same treatment as in the case of aspirin ulcer was applied, and the sum of the lengths (mm) of the mucosa damage generated at the glandular portion of the stomach was defined as the lesion index. The $ED_{50}$ value was calculated as described before.

4. Toxicity

For the toxicity, the test compounds were orally administered in the form of a 0.5% CMC suspension to 5 or 6 weeks old male ddY mice (i.e., 5 mice in each group) to determine the MLD (i.e., minimum lethal dose) thereof.

The results of antiulcer effects on various ulcer models and toxicity are shown in Table 3.

TABLE 3

| No. | $R^1$ | $R^2$ | Action on HCl—ethanol ulcer 30 mg/kg p.o. inhibition (%) | $ED_{50}$ mg/kg p.o. | Acid suppression 30 mg/kg i.d. inhibition (%) | Antistress ulcer 30 mg/kg p.o. inhibition (%) | MLD mg/kg p.o. |
|---|---|---|---|---|---|---|---|
| 1 | (isopentyl) | H | 100 | 5.9 | 53 | 79 | >1300 |
| 2 | (isopentyl) | CH₃ | 99 | — | 47 | 88 | — |
| 3 | (branched C8) | H | 100 | 2.8 | 57 | — | 1690 |
| 4 | (branched C8) | CH₃ | 100 | 3.0 | 56 | 92 | — |
| 7 | (cyclopentylmethyl, 5H) | H | 94.8 | — | 46.6 | — | — |
| 9 | (cyclohexyl, 6H) | H | 92.0 | — | 43.4 | — | — |
| 10 | (cyclohexyl, 6H) | CH₃ | 99.2 | — | — | — | — |
| 11 | (cyclohexylmethyl, 6H) | H | 100 | 5.8 | 50 | ($ED_{50}$ = 3 mg/kg P.O.) | 2856 |
| 12 | (cyclohexylmethyl, 6H) | CH₃ | 100 | 6.3 | 44 | 92 | — |

TABLE 3-continued

| No. | R¹ | R² | Action on HCl—ethanol ulcer 30 mg/kg p.o. inhibition (%) | ED$_{50}$ mg/kg p.o. | Acid suppression 30 mg/kg i.d. inhibition (%) | Antistress ulcer 30 mg/kg p.o. inhibition (%) | MLD mg/kg p.o. |
|---|---|---|---|---|---|---|---|
| 25 | 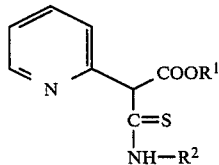 | H | 95.5 | — | 62.8 | — | — |
| Reference | —C$_2$H$_5$ | H | 74 | 11.0 | — | — | — |

As is clear from the results shown in Table 3, the 2-pyridylacetic acids having an R1 of C$_5$ to C$_{10}$ alkyl in the general formula (I) exhibits excellent antiulcer activities, especially superior to those having lower alkyl groups in R$^1$ of the formula (I).

I claim:

1. A 2-pyridylacetic acid derivative having the formula (I):

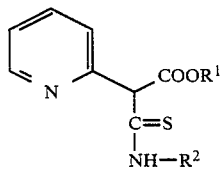

(I)

wherein R$^1$ represents an alkyl having 5 to 10 carbon atoms or —(CH$_2$)$_m$—cycloalkyl group having C$_5$–C$_8$ cycloalkyl, which is optionally substituted with 1 to 3 alkyl groups having 1 to 6 carbon atoms, where m represents zero or an integer of 1 to 4; R$^2$ represents hydrogen, a linear alkyl having from 1 to 10 carbon atoms, a cyclic alkyl having 3 to 10 carbon atoms, a hydroxylalkyl having 2 to 16 carbon atoms, an alkenyl having 3 to 6 carbon atoms, an aryl having 6 to 10 carbon atoms, an aralkyl having 7 to 15 carbon atoms, or a group (CH$_2$)$_n$—A, wherein n represents an integer of 0 to 3 and A represents a pyridine or piperidine ring, or a pharmacologically acceptable acid addition salt thereof.

2. A peptic ulcer therapeutical agent comprising a therapeutically effective amount of a 2-pyridylacetic acid derivative having the formula:

(I)

wherein R$^1$ and R$^2$ are as defined in claim 1, or and/or the pharmacologically acceptable acid addition salt thereof in admixture with an inert carrier.

3. A method for treating a peptic ulcer in an individual in need of such treatment, comprising administering to the individual a therapeutically effective amount of the compound as claimed in claim 1.

* * * * *